US 11,058,538 B2

(12) United States Patent
Longoria

(10) Patent No.: US 11,058,538 B2
(45) Date of Patent: Jul. 13, 2021

(54) SYNTHETIC CHORD FOR CARDIAC VALVE REPAIR APPLICATIONS

(71) Applicant: Charles Somers Living Trust, McClellan, CA (US)

(72) Inventor: James Longoria, Sacramento, CA (US)

(73) Assignee: Charles Somers Living Trust, McClellan, CA (US)

( * ) Notice: Subject to any disclaimer, the term of this patent is extended or adjusted under 35 U.S.C. 154(b) by 0 days.

(21) Appl. No.: 15/454,485

(22) Filed: Mar. 9, 2017

(65) Prior Publication Data
US 2017/0258592 A1 Sep. 14, 2017

Related U.S. Application Data

(60) Provisional application No. 62/306,578, filed on Mar. 10, 2016.

(51) Int. Cl.
*A61F 2/24* (2006.01)
*A61B 17/04* (2006.01)
*A61B 17/00* (2006.01)

(52) U.S. Cl.
CPC .......... *A61F 2/2457* (2013.01); *A61F 2/2436* (2013.01); *A61B 2017/00783* (2013.01);
(Continued)

(58) Field of Classification Search
CPC ........ A61B 17/0401; A61B 2017/0412; A61B 2017/0419; A61F 2/24; A61F 2/2427; A61F 2/2436; A61F 2/2457; A61F 2202/0016; A61F 2210/0014; A61F 2250/0064; A61F 2230/0091; A61F 2/2442
See application file for complete search history.

(56) References Cited

U.S. PATENT DOCUMENTS 5,002,563 A 3/1991 Pyka et al.
5,269,783 A 12/1993 Sander
(Continued)

FOREIGN PATENT DOCUMENTS

WO WO0230295 A1 4/2002
WO WO2004112658 A1 12/2004
(Continued)

OTHER PUBLICATIONS

Bizzarri et al., Different ways to repair the mitral valve with artificial chordae: a systematic review, Journal of Cardiothoracic Surgery, (2010), 5(22):1-6.
(Continued)

*Primary Examiner* — Sarah A Simpson
(74) *Attorney, Agent, or Firm* — Heisler & Associates

(57) ABSTRACT

Synthetic chord devices and methods for using the same for connecting tissues are provided. Aspects of the synthetic chord devices include a first flexible connector having first and second ends. Located at the first end is an attachment element that includes a tissue piercing member coupled to a securing member. The securing member includes an elongated shape memory coil that is present in a removable sheath configured to maintain elongation of the shape memory coil. A reinforcing element is located at the second end. The devices and methods of the invention find use in a variety of applications, such as cardiac valve, e.g., mitral valve, repair.

20 Claims, 5 Drawing Sheets

(52) U.S. Cl.
CPC . *A61B 2017/0406* (2013.01); *A61B 2017/048* (2013.01); *A61B 2017/0409* (2013.01); *A61B 2017/0419* (2013.01); *A61B 2017/0443* (2013.01); *A61B 2017/0464* (2013.01); *A61F 2/2466* (2013.01); *A61F 2210/0014* (2013.01); *A61F 2220/0016* (2013.01); *A61F 2230/0091* (2013.01); *A61F 2250/0064* (2013.01)

(56) References Cited

U.S. PATENT DOCUMENTS

| | | | |
|---|---|---|---|
| 5,350,060 | A | 9/1994 | Alpern et al. |
| 5,383,904 | A | 1/1995 | Totakura et al. |
| 5,500,000 | A | 3/1996 | Feagin et al. |
| 5,593,424 | A | 1/1997 | Northrup, III |
| 5,709,695 | A | 1/1998 | Northrup, III |
| 6,029,806 | A | 2/2000 | Cerwin et al. |
| 6,231,561 | B1 | 5/2001 | Frazier et al. |
| 6,358,277 | B1 | 3/2002 | Duran |
| 6,506,197 | B1 | 1/2003 | Rollero et al. |
| 6,514,265 | B2 | 2/2003 | Ho et al. |
| 6,607,541 | B1 | 8/2003 | Gardiner et al. |
| 6,613,059 | B2 | 9/2003 | Schaller et al. |
| 6,641,593 | B1 | 11/2003 | Schaller et al. |
| 6,797,002 | B2 | 9/2004 | Spence et al. |
| 6,913,607 | B2 | 7/2005 | Ainsworth et al. |
| 6,964,684 | B2 | 11/2005 | Ortiz et al. |
| 7,066,954 | B2 | 6/2006 | Ryan et al. |
| 7,963,973 | B2 | 6/2011 | Nguyen et al. |
| 8,147,542 | B2 | 4/2012 | Maisano et al. |
| 8,252,050 | B2 | 8/2012 | Maisano et al. |
| 8,303,622 | B2 | 11/2012 | Alkhatib |
| 9,700,412 | B2* | 7/2017 | Yaron ............... A61F 2/2442 |
| 2001/0018592 | A1 | 8/2001 | Schaller et al. |
| 2001/0041916 | A1 | 11/2001 | Bonutti |
| 2002/0029080 | A1 | 3/2002 | Mortier et al. |
| 2002/0165561 | A1 | 11/2002 | Ainsworth et al. |
| 2003/0078465 | A1 | 4/2003 | Pai et al. |
| 2003/0105519 | A1 | 6/2003 | Fasol et al. |
| 2003/0149447 | A1 | 8/2003 | Morency et al. |
| 2003/0171641 | A1 | 9/2003 | Schweich, Jr. et al. |
| 2004/0039392 | A1 | 2/2004 | Trieu |
| 2004/0044364 | A1 | 3/2004 | Devries et al. |
| 2004/0111099 | A1 | 6/2004 | Nguyen et al. |
| 2004/0225304 | A1 | 11/2004 | Vidlund et al. |
| 2005/0159810 | A1 | 7/2005 | Filsoufi |
| 2005/0192630 | A1 | 9/2005 | Maas et al. |
| 2005/0251159 | A1 | 11/2005 | Ewers et al. |
| 2005/0267531 | A1 | 12/2005 | Ruff et al. |
| 2006/0030885 | A1 | 2/2006 | Hyde |
| 2006/0052821 | A1* | 3/2006 | Abbott ............... A61B 17/0057 606/213 |
| 2006/0096877 | A1 | 5/2006 | Khajavi et al. |
| 2006/0106405 | A1 | 5/2006 | Fann et al. |
| 2006/0205995 | A1 | 9/2006 | Browning |
| 2007/0038249 | A1 | 2/2007 | Kolster |
| 2007/0049971 | A1 | 3/2007 | Chin et al. |
| 2007/0055303 | A1 | 3/2007 | Vidlund et al. |
| 2007/0066863 | A1 | 3/2007 | Rafiee et al. |
| 2007/0118151 | A1 | 5/2007 | Davidson |
| 2007/0118213 | A1 | 5/2007 | Loulmet |
| 2007/0173930 | A1 | 7/2007 | Sogard et al. |
| 2007/0173932 | A1 | 7/2007 | Cali et al. |
| 2007/0208377 | A1 | 9/2007 | Kaplan et al. |
| 2008/0009888 | A1 | 1/2008 | Ewers et al. |
| 2008/0051807 | A1 | 2/2008 | St. Goar et al. |
| 2009/0082806 | A1 | 3/2009 | West, Jr. et al. |
| 2009/0177274 | A1 | 7/2009 | Scorsin et al. |
| 2009/0216265 | A1 | 8/2009 | Devries et al. |
| 2009/0248067 | A1 | 10/2009 | Maiorino et al. |
| 2009/0312791 | A1 | 12/2009 | Lindh, Sr. et al. |
| 2010/0023118 | A1 | 1/2010 | Medlock et al. |
| 2010/0042147 | A1 | 2/2010 | Janovsky et al. |
| 2010/0121435 | A1 | 5/2010 | Subramanian et al. |
| 2010/0161042 | A1 | 6/2010 | Maisano et al. |
| 2010/0179574 | A1 | 7/2010 | Longoria et al. |
| 2010/0280603 | A1 | 11/2010 | Maisano et al. |
| 2010/0280604 | A1 | 11/2010 | Zipory et al. |
| 2010/0280605 | A1 | 11/2010 | Hammer et al. |
| 2010/0298929 | A1 | 11/2010 | Thornton et al. |
| 2011/0011917 | A1 | 1/2011 | Loulmet |
| 2011/0264208 | A1 | 10/2011 | Duffy et al. |
| 2012/0041548 | A1 | 2/2012 | Crabtree |
| 2012/0078355 | A1 | 3/2012 | Zipory et al. |
| 2012/0136436 | A1 | 5/2012 | Cabiri et al. |
| 2013/0006352 | A1* | 1/2013 | Yaron ............... A61F 2/2445 623/2.37 |
| 2013/0338764 | A1* | 12/2013 | Thornton ......... A61B 17/00234 623/2.11 |
| 2014/0114404 | A1 | 4/2014 | Gammie et al. |
| 2014/0364938 | A1 | 12/2014 | Longoria et al. |
| 2015/0045879 | A1* | 2/2015 | Longoria ........... A61B 17/0401 623/2.12 |
| 2015/0119934 | A1* | 4/2015 | Shluzas .............. A61B 17/0401 606/228 |
| 2017/0071733 | A1* | 3/2017 | Ghione ................. A61F 2/2412 |

FOREIGN PATENT DOCUMENTS

| | | |
|---|---|---|
| WO | WO2005011463 A2 | 2/2005 |
| WO | WO2009046126 A1 | 4/2009 |
| WO | WO2010073246 A2 | 7/2010 |
| WO | WO2010083103 A1 | 7/2010 |
| WO | WO2010128502 A1 | 11/2010 |
| WO | WO2010128503 A2 | 11/2010 |
| WO | WO2012137208 A1 | 10/2012 |
| WO | WO2014197620 A1 | 12/2014 |
| WO | WO2015020816 A1 | 2/2015 |

OTHER PUBLICATIONS

Chiappini et al., Replacement of chordae tendineae with polytetrafluoroethylene (PTFE) sutures in mitral valve repair : early and long-term results, J Heart Valve Dis. Sep. 2006; 15(5):657-663 Abstract.

Cook et al., Significant reduction in annuloplasty operative lime with the use of nitinol clips in robotically assisted mitral valve repai; J. Thorac Cardiovasc. Surg. May 2007; 133(5):12,64-67.

Duran et al., Techniques for ensuring hte correct length of new mitral chords; J Heart Valve Disease Mar. 2003; 12 (2)156-161.

Sillinov et al., Pre-Measured Artificial Chordae for MV Repair; Annals of Thoracic Surgery Aug. 2007; 84: 2127-2129.

Kuntz et al., Early and mid-term results of mitral valve repair using premeasured Gore-Tex loops ('loop technique'); Eur J Cariothorac Surg. Apr. 2008; 33(4):566-572; Epub Feb. 12, 2008.

Maisano et al., Beating-heart implantation of adjustable length mitral valve chordae: acute and chronic experience in an animal model, European Journal of Cardio-thoracic Surgery, (2011), 40(4):840-847.

Maisano et al., Neochordae Implantation Made Easy With an Adjustable Device, Innovations, (2010), 5(4):287-290.

Maselli et al., A New Method for artificial chordae length "tuning" in mitral valve repair: Preliminary Experience; J. Thorac Cardiovas. Surgery Aug. 2007; 134:454-459.

Smith et al., Endoscopic placement of multiple artificial chordae with robotic assistance and nitinol clip fixation; J. Thorac Cardiovasc. Surgery Mar. 2008; 135(3):610-614.

Tomita et al., Surgical application for a prolapse of the anterior mitral leaflet by replacing artificial chordae with polytetraflouroethylene grails; Surg. Today; (2005) 35(10):81 2-8 Abstract.

Zussa et al., Artificial chordae in the treatment of anterior mitral leaflet pathology; Cardiovasc. Surgery Feb. 1997; 5 (1):125-128 Abstract.

* cited by examiner

SYNTHETIC CHORD FOR CARDIAC VALVE REPAIR APPLICATIONS

CROSS-REFERENCE TO RELATED APPLICATIONS

Pursuant to 35 U.S.C. § 119 (e), this application claims priority to the filing date of the U.S. Provisional Patent Application Ser. No. 62/306,578 filed Mar. 10, 2016; the disclosures of which applications are herein incorporated by reference.

INTRODUCTION

The mitral valve is composed of two leaflets attached to the mitral valve annulus, which are supported at the free edge by chordae tendineae (chords) attached to the inside wall of the left ventricle and to the papillary muscles. However, sometimes one or both of the valve leaflets become loose, due to loosening or failure of one or more of these chords. The valve then prolapses, and the seal that it normally provides between the left atrium and left ventricle becomes compromised, causing the blood to flow back into the left atrium during systole.

A variety of methods have been described for placement of artificial chordae tendineae to correct mitral valve leaflet prolapse and treat diseased mitral valve chordae tendineae. However, there are many technical challenges in this surgical procedure, especially when performed with minimally invasive techniques. The most common method of repairing the valves is to create synthetic chordae tendineae from polytetrafluoroethylene (PTFE), which tendineae are fastened into place between the papillary muscle of the heart wall and the mitral valve leaflets. Cardiac surgeons usually are required to perform the time-consuming process of measuring and cutting the necessary length of synthetic chordae tendineae material during the surgical procedure after they have measured the dimensions of the patient's heart valves. In addition, anchoring the synthetic chordae tendineae in the papillary muscle and securing the fasteners through the leaflets is often technically difficult in minimally invasive procedures, because of limitations in using 2-dimensional video for viewing the surgical field, limited exposure of the surgical field, and limited degrees of freedom using standard thoracoscopic instrumentation.

SUMMARY

Synthetic chord devices and methods for using the same for connecting tissues are provided. Aspects of the synthetic chord devices include a first flexible connector having first and second ends. Located at the first end is an attachment element that includes a tissue piercing member coupled to a securing member. The securing member includes an elongated shape memory coil that is present in a removable sheath configured to maintain elongation of the shape memory coil. A reinforcing element is located at the second end. The devices and methods of the invention find use in a variety of applications, such as cardiac valve, e.g., mitral valve, repair.

DEFINITIONS

Figure 1A:
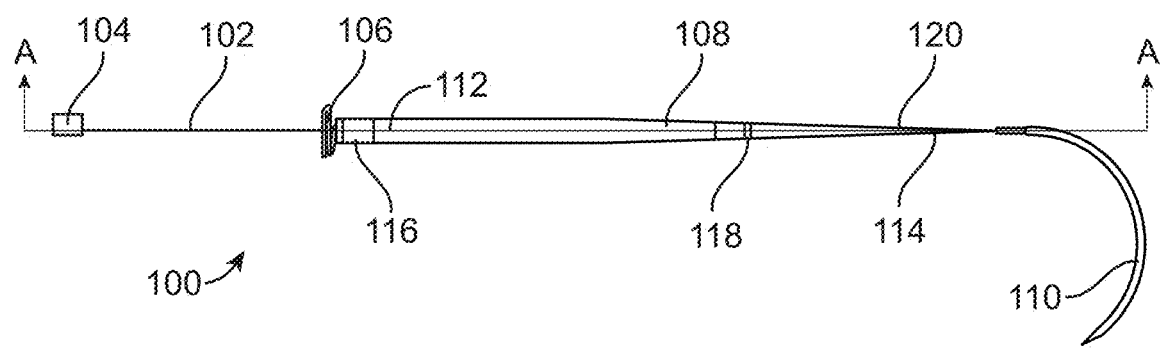
FIGS. 1A and 1B provide side and top views of a synthetic chord device of the invention prior to deployment.

As used herein, the term "tissue" refers to one or more aggregates of cells in a subject (e.g., a living organism, such as a mammal, such as a human) that have a similar function and structure or to a plurality of different types of such aggregates. Tissue may include, for example, organ tissue, muscle tissue (e.g., cardiac muscle; smooth muscle; and/or skeletal muscle), connective tissue, nervous tissue and/or epithelial tissue.

The term "subject" is used interchangeably in this disclosure with the term "patient". In certain embodiments, a subject is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, subjects are humans. The term "humans" may include human subjects of both genders and at any stage of development (e.g., fetal, neonates, infant, juvenile, adolescent, adult), where in certain embodiments the human subject is a juvenile, adolescent or adult. While the devices and methods described herein may be applied to perform a procedure on a human subject, it is to be understood that the subject devices and methods may also be carried out to perform a procedure on other subjects (that is, in "non-human subjects").

The present disclosure provides embodiments of devices (e.g., a synthetic chord device or a portion thereof, such as a flexible connector, an attachment element, a tissue piercing member, a securing member and/or a reinforcing element) that are implantable. As used herein, the terms "implantable", "implanted" and "implanting" refer or relate to the characteristic of the ability of a device to be placed (e.g., surgically introduced) into a physiological site (e.g., a site within the body of a subject) and maintained for a period of time without substantial, if any, impairment of function. As such, once implanted in or on a body, the devices do not deteriorate in terms of function, e.g., as determined by ability to perform effectively as described herein, for a period of 2 days or more, such as 1 week or more, 4 weeks or more, 6 months or more, or 1 year or more, e.g., 5 years or more, up to and including the remaining lifetime or expected remaining lifetime of the subject or more. Implantable devices may also be devices that are configured (e.g., dimensioned and/or shaped) to fit into a physiological site (e.g., a site within the body of a subject). For example, in certain embodiments, an implantable device may have a longest dimension, e.g., length, width or height, ranging from 0.05 mm to 150 mm, such as from 0.1 mm to 10 mm, including from 0.5 mm to 5 mm. Implanting may also include securing an implanted object (e.g., a prosthetic device) to one or more tissues within the body of the subject. Additionally, implanting may, in some instances, include all of the surgical procedures (e.g., cutting, suturing, sterilizing, etc.) necessary to introduce one or more objects into the body of a subject.

In some instances, the devices or portions thereof may be viewed as having a proximal and distal end. The term "proximal" refers to a direction oriented toward the operator during use or a position (e.g., a spatial position) closer to the operator (e.g., further from a subject or tissue thereof) during use (e.g., at a time when a tissue piercing device enters tissue). Similarly, the term "distal" refers to a direction oriented away from the operator during use or a position (e.g., a spatial position) further from the operator (e.g., closer to a subject or tissue thereof) during use (e.g., at a time when a tissue piercing device enters tissue). Accordingly, the phrase "proximal end" refers to that end of the device that is closest to the operator during use, while the phrase "distal end" refers to that end of the device that is most distant to the operator during use.

In certain variations of the disclosed methods and associated devices, the method, such as a method by which a synthetic cord device is used, is an open surgical procedure. As used herein, the phrase "open surgical procedure" refers to a surgical procedure wherein at least one long incision (e.g., having a length of 10 cm) is made in the body of a subject to introduce at least one surgical instrument and/or visualize the surgery through the incision. In an open surgical procedure, closure devices, e.g., staples, sutures, etc., may be used to close at least one incision.

In certain variations of the disclosed methods, the method is a minimally invasive surgical procedure. As used herein, the phrase "minimally invasive surgical procedure" refers to a surgical procedure that is less invasive than an open surgical procedure. A minimally invasive surgical procedure may involve the use of arthroscopic and/or laparoscopic devices and/or remote-control manipulation of surgical instruments. Minimally invasive surgical procedures include endovascular procedures, which may be totally endovascular procedures, percutaneous endovascular procedures, etc. Endovascular procedures are procedures in which at least a portion of the procedure is carried out using vascular access, e.g., arterial access.

Furthermore, the definitions and descriptions provided in one or more (e.g., one, two, three, or four, etc.) sections of this disclosure (e.g., the "Descriptions", "Devices", "Methods" and/or "Kits" sections below) are equally applicable to the devices, methods and aspects described in the other sections.

DETAILED DESCRIPTION

Synthetic chord devices and methods for using the same for connecting tissues are provided. Aspects of the synthetic chord devices include a first flexible connector having first and second ends. Located at the first end is an attachment element that includes a tissue piercing member coupled to a securing member. The securing member includes an elongated shape memory coil that is present in a removable sheath configured to maintain elongation of the shape memory coil. A reinforcing element is located at the second end. The devices and methods of the invention find use in a variety of applications, such as cardiac valve, e.g., mitral valve, repair.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Additionally, certain embodiments of the disclosed devices and/or associated methods can be represented by drawings which may be included in this application. Embodiments of the devices and their specific spatial characteristics and/or abilities include those shown or substantially shown in the drawings or which are reasonably inferable from the drawings. Such characteristics include, for example, one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal; distal), and/or numbers (e.g., three surfaces; four surfaces), or any combinations thereof. Such spatial characteristics also include, for example, the lack (e.g., specific absence of) one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal), and/or numbers (e.g., three surfaces), or any combinations thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Devices

As summarized above, aspects of the invention include synthetic chord devices. Synthetic chord devices as described herein are devices that are configured to connect or align tissues, or connect tissue to a prosthesis, or a combination thereof. The devices may be used in endovascular, minimally invasive surgical, open surgical, or other interventional procedures. Devices as described herein may be configured to secure a valve leaflet, such as a mitral valve leaflet or tricuspid valve leaflet, to a papillary muscle. When an aspect (e.g., a tissue, such as a valve leaflet) is secured, it may, for example, be retained at the same position or substantially at the same position (e.g., a position within the body of a subject) for a time period, such as a for a period of days, weeks, months, years and/or for at least the remaining lifetime of a subject.

Synthetic chord devices as described herein include a flexible connector (e.g., a first flexible connector, such as a flexible cord). The flexible connector has a first end and a second end. Embodiments of the synthetic chord devices include an attachment element at the first end of the first flexible connector. Attachment elements as described herein include a tissue piercing member coupled to a securing member. In some embodiments, the securing member attaches the first end of the flexible connector to a tissue location (e.g., a first tissue), following deployment of the securing member, e.g., as described in greater detail below. A portion of the flexible connector can be configured to be secured to a second tissue location. In some instances, the flexible connector is secured to the second tissue by a reinforcing element at the second end of the flexible connector. Various aspects of the embodiments of the devices, including the flexible connector, the attachment element (including the tissue piercing member and securing member) and the reinforcing element, are now described in greater detail below.

Flexible Connector

A synthetic chord device of certain embodiments of the subject invention includes a synthetic, or artificial, flexible connector, such as a flexible cord, line, filament, etc., which has an attachment element at one end of the connector for attaching the connector to a tissue. In some embodiments, the flexible connector is configured to be attached to a prosthesis, or to a device that substitutes for or supplements a missing or defective part of the body, e.g., a synthetic cardiac valve, or a porcine valve. In some embodiments, a synthetic chord is configured to be used as a synthetic chorda tendineae for use in repair of a cardiac valve, e.g., the mitral valve.

The flexible connector (e.g., the first flexible connector) element of the subject invention is a flexible elongated structure having a first end and a second end. The flexible connector may be made up of a single line or filament, e.g., thread, or two or more such lines, which may, where desired, be twisted about each other, e.g., as present in a yarn. As such, the flexible connector may have a single strand, or multiple strands, such as two strands, where the strands may or may not be twisted about each other. In certain embodiments, the first and second ends of the first flexible connector are not connected (e.g., do not form a continuous body of material or adjoin). As such, the first flexible connector does not form (e.g., is not shaped as) a loop (e.g., a continuous loop of one or more materials). In yet other instances, e.g., as described in greater detail below, the flexible connector may be made up of two filaments which are connected at the proximal and distal ends. In some embodiments, the flexible connector does not include a knot. By "knot" as used herein is meant an interlacement (e.g., looping) or entanglement of portions of a body (e.g., a flexible connector) that forms a knob or lump. In some aspects, a knot prevents a body (e.g., a longitudinal, round body, such as a cord) having the knot from traveling through an opening in an aspect having an area that is slightly larger than the cross sectional area of the body. In some aspects, a knot is created by tying (e.g., purposefully tying) a body into an interlaced configuration.

The first flexible connector element has a length (e.g., length between the first and second end) suitable for extending from a first tissue to a second tissue, such that the flexible connector may be secured to both the first and the second tissue. In some embodiments, the flexible connector element has a length suitable for extending from a first tissue (e.g., a mitral valve leaflet) to where it is secured to a second tissue (e.g., a papillary muscle). The length of the first flexible connector may vary, and in some instances ranges from 5 mm to 100 mm, such as from 5 mm to 25 mm, including 10 mm to 20 mm. In some embodiments, the first or second end of the first flexible connector can be secured to a prosthesis, or other device that substitutes for or supplements a missing or defective part of the body, e.g., a synthetic cardiac valve, or a porcine valve, which is located at the target tissue location.

In certain embodiments, the first flexible connector is constructed of one or more materials suitable for use in the body and that can be used in the methods of the subject invention, e.g., attaching a valve leaflet to the underlying cardiac tissue (e.g., attaching for an extended period of time, such as for the lifetime of the subject, without breaking). The flexible connector (e.g., the first flexible connector) can be made of a variety of materials. Such materials may be flexible materials. By "flexible", as used herein is meant pliable or capable of being bent or flexed repeatedly (e.g., bent or flexed with a force exerted by a human hand or other body part) without damage (e.g., physical deterioration). A flexible material may be a material that remains able to perform intended function (e.g., repeatedly flexing) by remaining pliable for at least the expected lifetime or useful lifetime of the aspect which the material is included in. In some embodiments, the flexible connector may include biocompatible materials. The phrase "biocompatible materials" are materials that can be placed on or in living tissue for an extended period of time, such as for a period of 2 days or more, such as 1 week or more, 4 weeks or more, 6 months or more, or 1 year or more, e.g., 5 years or more, up to and including the remaining lifetime or expected remaining lifetime of the subject or more, and not cause a significant adverse (e.g., detrimental to health) reaction (e.g., an immune response) in the tissue or the associated organism.

Biocompatible materials, as included in the subject devices, can include any suitable biocompatible material, which material may or may not be biodegradable. Biocompatible materials of the subject devices, in some instances, are polymeric materials (e.g., materials having one or more polymers) and/or metallic materials. Such materials may have characteristics of flexibility and/or high strength (e.g., able to withstand significant force, such as a force exerted on it by a tissue within a human body, without breaking and/or resistant to wear) and/or high fatigue resistance (e.g., able to retain its physical properties for long periods of time regardless of the amount of use or environment). Biocompatible materials may also include any of the shape memory materials listed herein, as described in greater detail below.

In some embodiments, biocompatible polymeric materials of the subject devices, include, but are not limited to: polytetrafluoroethene or polytetrafluoroethylene (PTFE), including expanded polytetrafluoroethylene (e-PTFE), polyester (Dacron™), nylon, polypropylene, polyethylene, high-density polyethylene (HDPE), polyurethane, and combinations or mixtures thereof. Similarly, in certain embodiments, biocompatible metallic materials of the subject devices, include, but are not limited to: stainless steel; titanium; shape memory alloys, e.g., a nickel-titanium (NiTi) alloy (e.g., nitinol), a nickel-cobalt alloy, such as ELGILOY® cobalt-chromium-nickel alloy; tantalum, and combinations or mixtures thereof.

In certain embodiments, an active agent may be included in the composition of a biocompatible material, such as a polymeric material. As used herein, the phrase "active agent" refers to one or more chemical substances that, when administered to (e.g., placed in contact with or ingested by) a human, have one or more physiological effects. In some embodiments, the one or more active agents include an antithrombotic substance and/or an antibiotic substance and/or an anti-inflammatory (e.g., a substance that reduces or prevents inflammation). In various embodiments, a first flexible connector may be coated with a polymer, such as a polymer that releases one or more active agents (e.g., an anticoagulant that thereby reduces the risk of thrombus formation).

The cross-sectional configuration of the first flexible connector can be any suitable shape, such as round, oval, rectangular, square, etc. In some instances, the first flexible connector may have a flattened cross-sectional shape, such as a "ribbon" shape. In other embodiments, the flexible connector may be a combination of shapes, such as for example, a flexible connector that is round on two sides with a flat surface on the opposing two sides. In some embodiments the entire flexible connector has the same shape, and in other embodiments, at least a portion of the flexible connector may have a different shape, e.g., a ribbon configuration, or at least a portion of the connector that is flattened, or has a flat surface.

In some embodiments, the greatest outer diameter of the flexible connector (or a strand of the flexible connector where the flexible connector includes two or more strands) ranges from 0.1 mm to 1.0 mm, such as from 0.1 mm to 0.5 mm, or 0.15 mm to 0.25 mm. In some embodiments, the entire flexible connector has the same diameter. In other embodiments, at least a portion of the connector has a different diameter, e.g., a smaller diameter. In some embodiments, at least a portion of the connector may have both a different configuration and a different diameter, e.g., a portion of the connector may have a flat surface, where the portion of the connector having a flat surface has a largest outer diameter larger than the remainder of the connector.

A portion of the flexible connector (e.g., the first flexible connector) at the first end and/or second end is configured to be secured to tissue, such as cardiac tissue located below a cardiac valve leaflet. In some embodiments, a portion of the flexible connector at the first end and/or second end can be secured to a prosthesis, or other device that substitutes for or supplements a missing or defective part of the body. The portion of the flexible connector at the first end and/or second end that is configured to be secured to tissue can have the same shape and diameter as the remainder of the flexible connector, or in some embodiments it may have a different shape or diameter as the remainder of the flexible connector, as in the embodiments discussed above. For example, the portion of the connector at the first end and/or second end that is configured to be attached to a tissue (e.g., a first or second tissue) may be flattened, or have a smaller or larger diameter.

Attachment Element

The synthetic chord devices further include an attachment element located at an end (e.g., the first end) of a flexible connector. The attachment element is configured to attach a flexible connector (e.g., a first flexible connector), such as those described above, to a tissue, e.g., a cardiac valve leaflet, or prosthesis, as desired. In some instances, an attachment element is an element that includes a tissue piercing member and a securing member. The attachment element may be configured such that the tissue piercing member is attached to the securing member directly (e.g., the tissue piercing member is retained in direct contact with the tissue securing member) or, in some embodiments, with a second flexible connector (e.g., a second flexible member, e.g., which may be in the form of a line, filament, hypotube, etc., such as described in greater detail below).

A tissue piercing member may, in some embodiments, be release-ably coupled to a securing member. In other embodiments, the attachment element may be configured such that a tissue piercing member is attached to a second flexible connector, which in turn is release-ably coupled to the securing member. In some embodiments, the attachment element can be secured to a prosthesis, or other device that substitutes for or supplements a missing or defective part of the body.

A second flexible connector as discussed herein, can be formed from any suitable biocompatible material such as cotton, nylon, polyester, polypropylene, polyglycolic acid, polylactide, lactic acid, trimethlylene carbonate, polycaprolactone, or polydiaxanone or copolymers or homopolymers thereof, or a metal alloy, such as Nitinol shape memory or stainless steel, a polymeric material, or any other suitable material, such as the biocompatible materials listed herein, including the shape memory materials listed herein, and equivalents thereof. The material of the second flexible connector may be non-stretchable or stretchable, and have various cross-sectional diameters. In some embodiments, the second flexible connector does not include a knot. In some embodiments, the second flexible connector does not form a loop (e.g., does not form a continuous band of material). In some instances, the second flexible connector may have a cross-sectional diameter ranging from 0.1 mm to 1.0 mm. The diameter of a second flexible connector will vary depending on the specific application. Additionally, the length of the second flexible connector may vary, and in some instances range from 5 mm to 100 mm, such as from 5 mm to 25 mm, or 10 mm to 20 mm. A second flexible connector may have a different length (e.g., shorter or longer) than the length of the first flexible connector or the same length as the first flexible connector.

The second flexible connector may be attached to the piercing member by crimping or swaging or otherwise attaching the piercing member or needle onto the second flexible connector, gluing the second flexible connector to the piercing member or needle, or any other suitable attachment method. Second flexible connectors can also have various cross-sectional shapes, such as round, oval, etc. Additionally, second flexible connectors, in certain variations, may have any of the physical characteristics (e.g., compositions and/or dimensions, etc.) set forth for any of the connectors described herein (e.g., the first flexible connectors) or any combination of such characteristics.

A tissue piercing member is any device that can be used to pierce through tissue, e.g., a needle. In some embodiments, the piercing member can also be used to pierce a prosthesis, e.g., a synthetic valve. Piercing members of interest include needles, wires, etc. Needles of interest include conventional cardiac surgical needles and equivalents thereof. Suitable surgical needles can be manufactured from stainless steel, a stainless steel alloy, or any other suitable material, such as a polymeric material. The material can also have special coatings and sharpening methods that facilitate atraumatic tissue penetration. The shapes and sizes of the surgical needles can vary with the type and design of the needle. In some embodiments, the needles may be permanently "swaged" or attached to a fastening cord or material. In some embodiments, the fastening cord or material may be designed to come off the needle with a sharp straight tug (e.g., "pop-offs").

Suitable lengths for the piercing members that are in the form of a needle can range in some embodiments from 5 mm to 50 mm, such as from 5 mm to 45 mm, including 5 mm to 25 mm. The diameter of the piercing member ranges in some embodiments from 0.05 mm to 2.0 mm, e.g., 0.05 to 1.0 mm, such as from 0.05 mm to 0.5 mm, including 0.1 mm to 0.5 mm. In some embodiments, the diameter of at least a portion of a piercing member is greater than the diameter of an attached second flexible connector and/or attached securing member, coupled so that the attached second flexible connector and/or attached securing member can easily be pulled through an opening formed in a tissue (or other material) by the piercing member, e.g., the needle. The distal end or tip of the piercing member can be rigid to facilitate penetration of tissue. The remaining length of the piercing member can be rigid or flexible to facilitate movement of the piercing member through the tissue or other material. The piercing member tips can have various configurations and can, for example, have a piercing point, tapered point, or have a cutting or reverse cutting configuration for example, and have a shape such as conical, tapered, or grounded to attain a three or four facet tip. Piercing members can have any suitable shape or radius of curvature. Piercing members can have any suitable cross-sectional shape that may vary in different sections of the needle, e.g., round, rectangular, etc. In some embodiments, the piercing member can also be integrally formed with the second flexible connector (e.g., both piercing member and second flexible connector formed of the same material). Also, in some embodiments, the subject devices include only one tissue piercing member.

The attachment elements of the subject devices also include a securing member. A securing member is any device that can be used in a surgical, endovascular, or other interventional procedure that can be used to secure a flexible connector, (e.g., a first flexible connector, and/or an artificial mitral valve chorda tendineae). By "secure" is meant that the securing member provides for stable association of the end of the flexible connector to the target tissue location, e.g., mitral valve leaflet. By "stable association" is meant that the end of the flexible connector is substantially if not completely fixed relative to the tissue location of interest such that when the end of the flexible connector moves, the target tissue location to which it is secured by the deployed securing member also moves. In some embodiments, the disclosed devices include only one securing member. In some embodiments, the securing member of a synthetic chord device is located at, and/or attached to (e.g., releaseably attached to), the first end of a first flexible connector of the device. To provide for the above functionality, the securing member may, in some instances, be stably associated with the first end of the flexible connector. As the securing member is stably associated with the first end of the flexible connector, the attachment site of the securing member to the first end of the flexible connector is fixed under physiological, e.g., beating heart, conditions, such that the securing member at the attachment site does not move relative to the first end of the flexible connector at the attachment site.

Securing members of devices of the invention include an elongated shape memory coil that is present in a removable sheath configured to maintain elongation of the shape memory coil prior to deployment. The elongated shape memory coil is a coil that includes a shape memory material, where the coil is present in a deformed or elongated configuration, such that it is linear and not helical. The elongated shape memory coil is one that is held in a non-helical, e.g., linear configuration, by a removable sheath, e.g., as described below. When present in the elongated or tensioned configuration, the length of the coil may vary, ranging in some instances from 1 to 200 mm, such as 25 to 75 mm. When present in a relaxed or non-tensioned state, the elongated shape memory coil is configured to assume a stacked, multi-loop configuration. By stacked, multi-loop configuration is meant that the coil is made up of two more loops which are configured such that one loop is above another loop. While the number of loops present in the stacked, multi-loop coil may vary, in some instances the number ranges from 2 to 6, such as 2 to 4, e.g., 2 to 3, where in some instances the coil has 2 distinct loops. While the dimensions of the shape memory coil may vary, in some instances the shape memory coil is made up of a wire having an outer dimension ranging from 0.025 to 0.5, such as 0.12 to 0.25 mm. In the non-elongated or relaxed state, e.g., when not held in a linear configuration by the removable sheath, the dimensions of a given loop of the coil may vary, where in some instances a given loop has an outer diameter ranging from 0.5 to 6, such as 2 to 4 mm. The loop to loop separation distance between any two loops in the stacked, multi-loop coil, i.e., the stack distance, may vary, where in some instance the stacked loops have a loop to loop separation distance ranging from 0.012 to 2 mm. When present in the relaxed state, the height of the stacked, multi-loop coil may vary, ranging in some instances from 0.05 to 3.5, such as 0.2 to 0.7 mm. The loops may have the same or different orientations, including opposing orientations, as desired.

As the coil is a shape memory coil, it is fabricated from a shape memory material. Shape memory materials that may be employed in embodiments of the devices include shape memory polymers (SMPs), shape memory alloys (SMAs), etc. Shape memory materials of interest include shape memory metal alloys, such as alloys of nickel (e.g., nickel titanium alloy (nitinol), nickel cobalt alloys (e.g., ELGILOY® cobalt-chromium-nickel alloy, etc.), zinc, copper (e.g., CuZnAl), gold, iron, etc. Also of interest are non-metallic materials that exhibit shape memory qualities, e.g., shape memory plastics, etc.

In some instances, aspects of the securing members further include a casing associated with the elongated shape memory coil, such that the elongated shape memory coil may be described as being an encased elongated shape memory coil. The casing is a covering structure that extends along at least a portion of the elongated shape memory coil, and is configured to provide for a compatible association between the securing member and tissue when the securing member is in a deployed state. In some instances, the casing has a structure and/or is fabricated from a material that promotes tissue ingrowth into the securing member following deployment, thereby ensuring a stable associated between the securing member and the tissue. For example, the casing may have a braided structure. As the casing extends along at least a portion of the elongated shape memory coil, it extends 10% or more, including 25% or more, such as 50% or more, including 75% or more, such as 90% or more, up to 100% of the length of the shape memory coil, where in some instances the length of the casing may be longer than the shape memory coil. The casing may have a variety of different configurations, where in some instances the configuration is one that increases the tissue contact area of the securing member as compared to just the wire component of the securing member by an amount that provides for the desired compatible association. In some instances, the casing is configured as a sleeve or sheath that extends at least partially along the length of the coil. In these embodiments, the dimensions of the sleeve may vary, where in some instances the sleeve has an inner diameter ranging from 0.025 to 1.0, such as 0.2 to 0.4 mm and an outer diameter ranging from 0.05 to 2.0, such as 0.30 to 0.80 mm. The thickness of the sleeve wall may also vary, ranging in some instances from 0.01 to 0.50, such as 0.05 to 0.25 mm. In some instances, the casing is configured as a ribbon that extends at least partially along the length of the coil. In these embodiments, the dimensions of the ribbon may vary, where in some instances the ribbon has width ranging from 0.012 to 1.8, such as 0.1 to 0.25 mm. The thickness of the ribbon may also vary, ranging in some instances from 0.012 to 0.5, such as 0.1 to 0.25 mm. Where the casing has a ribbon configuration, the shape memory coil may be positioned along a side of the ribbon, down the middle of the ribbon, or along some axis between a side and the middle of the ribbon, as desired.

As the casing is configured to provide for a compatible association between tissue and the securing member upon deployment of the securing member, e.g., so that the deployed securing member does not tear into or lacerate the tissue, in some instances the casing comprises a biocompatible flexible material. Flexible materials that may be used for the casing may vary, where in some instances materials employed for the casing are ones that have a Young's modulus of 1 GPa or less, such as 0.7 GPa or less, including 0.5 GPa or less, for instance, 0.3 GPa or less, or 0.1 GPa or less, such as 0.05 GPa or less, or 0.01 GPa or less. In some embodiments, the casing includes a biocompatible polymeric material, where such materials include, but are not limited to: polytetrafluoroethene or polytetrafluoroethylene (PFTE), including expanded polytetrafluoroethylene (e-PFTE), polyester (Dacron™), nylon, polypropylene, polyethylene, high-density polyethylene (HDPE), polyurethane, and combinations or mixtures thereof.

In addition to the encased elongated shape memory coil, the securing member further includes a removable sheath configured to maintain elongation of the shape memory coil. In some instances, the removable sheath is an elongated tubular structure having a proximal and distal end, where the sheath is configured to maintain elongation of the shape memory coil when present inside of the sheath. The dimensions of the sheath may vary as desired, where in some instances the outer diameter of the sheath ranges from 0.05 to 3.0, such as 0.10 to 1.0 mm and the inner diameter of the sheath ranging from 0.03 to 2.0, such as 0.45 to 1.0 mm. The length of the sheath may also vary, ranging in some instances from 1 to 200, such as 15 to 70 mm. The sheath may be fabricated from any convenient material, where materials of interest include, but are not limited to, biocompatible polymeric material, where such materials include, but are not limited to: polytetrafluoroethene or polytetrafluoroethylene (PFTE), including expanded polytetrafluoroethylene (e-PFTE), polyester (Dacron™), nylon, polypropylene, polyethylene, high-density polyethylene (HDPE), polyurethane, and combinations or mixtures thereof. While the configuration of the sheath may vary, upon removal of the sheath, the elongated shape memory coil assumes its relaxed, coiled state, since the tension imparted on the coil by the sheath that maintains the coil in the elongated state has been removed. Where desired, the sheath may include one or more markings, such as orientation markers, on an outer surface thereof. The markings may take any convenient configuration, such as bands or strips of different colors, etc.

The securing member transitions from a linear to a coiled configuration upon separation of the tissue piercing member component (which may be just the tissue piercing member or the tissue piercing member and a second flexible connector, e.g., as described above) from the attachment element and removal of the flexible sheath. As such, following initial placement of the synthetic chord device at the desired anatomical location, separation of the tissue piercing member (and second flexible connector, if present) from the securing member and removal of the sheath results in a change in configuration of the securing member from a linear to coiled configuration (i.e., from the tensioned to the relaxed state).

Upon deployment, the loop of the coil which is adjacent the surface of the tissue that is distal from the flexible connector may be configured to cover a surface of the tissue sufficient to secure the first end of the flexible connector to the tissue, e.g., such that the first end can no longer be pulled through the tissue. In some instances, the surface area of the tissue covered by the first loop upon deployment ranges from 0.5 mm$^2$ to 50 mm$^2$, such as 2 mm$^2$ to 25 mm$^2$, e.g., 5 mm$^2$ to 20 mm$^2$. In some instances, the securing member has a low-profile upon deployment. By "low-profile" is meant that the top of the loop when deployed is not located at a substantial height relative to the surface of the target tissue to which it is secured. While the height of a given low profile loop may vary, in some instances the height ranges from 0.5 to 5 mm, such as 0.05 to 2.5 mm, e.g., 1 to 2 mm, above the surface of the target tissue to which it is secured.

Upon deployment, the relaxed coil also includes at least a second loop on the tissue surface opposite that with which the first loop is associated, e.g., as described above. In other words, the deployed shape memory coil (which is present in the relaxed state) includes at least a second loop which associated with the tissue surface that is proximal to the flexible connector. In some instances, the surface area of the tissue covered by the second loop upon deployment ranges from 0.5 mm$^2$ to 50 mm$^2$, such as 2 mm$^2$ to 25 mm$^2$, e.g., 5 mm$^2$ to 20 mm$^2$. As with the first loop, in some instances the second loop has a low-profile upon deployment, e.g., as described above.

Where desired, the securing member may further include one or more features that serve to maintain the stable association of the relaxed coil with the tissue, e.g., by stabilizing the coil structure in the relaxed state. While these maintenance features may vary, maintenance features of interest include, but are not limited to: barbs, hooks, etc.

As discussed above, the securing member may be releaseably coupled to a tissue piercing member, where release of the tissue piercing member from the securing member and subsequent removal of the sheath causes the securing member to transition from a linear to coiled configuration, e.g., as described above. In some embodiments, a second flexible connector is provided between a tissue piercing member of a device and a securing member. In such a configuration, the securing member and tissue piercing member of an attachment element of the device are separated from each other by the second flexible connector. Such a configuration may, for example, facilitate threading the securing member. In some instances, the distal end of the sheath is stably associated with the second flexible connector.

Separation of the tissue piercing member from the securing member and removal of the sheath may be achieved using any convenient protocol. For example, the tissue piercing member may be separated from the securing member using shears, a scalpel or other convenient cutting device, as desired, following by removal of the sheath from the coil to deploy the coil.

Reinforcing Element

The portion of the first flexible connector at the end (e.g., the second end) that is configured to be secured to tissue can include a reinforcing element (e.g., a reinforcing member) attached thereto. A reinforcing element is a member that disperses the force of the securing flexible connector over a larger surface area. The area over which the force is dispersed by the reinforcing element may vary so long as it is sufficient to secure the second end of the flexible connector to the tissue location of interest (e.g., papillary muscle), and in some instances ranges from 0.5 mm$^2$ to 50 mm$^2$, such as 2 mm$^2$ to 25 mm$^2$, e.g., 5 mm$^2$ to 20 mm$^2$, and in some embodiments ranges from 0.5 to 25 mm$^2$, such as 1 to 20 mm$^2$, including 1 to 10 mm$^2$.

In various embodiments, the reinforcing element is integral with the first flexible connector. The term "integral," as used herein, refers to the characteristic of being integrated with or composed of a continuous piece of one or more materials as another aspect. For example, one integral aspect may not be separated from another integral aspect by a particular adjoining surface.

In some embodiments, the reinforcing element is a separate element (e.g., composed of a body, such as a body of material, that is a different body than that of the first flexible connector) than the flexible connector and is attached to the first flexible connector. In embodiments in which the reinforcing element is a separate element from the first flexible connector, the reinforcing element includes at least one surface that may abut at least one surface of the first flexible connector. In embodiments in which the reinforcing element is a separate element from the first flexible connector, the reinforcing element may be moved with respect to (e.g., toward, away from, or along) the first flexible connector.

In some embodiments of the subject devices in which the reinforcing element is a separate element than the first flexible connector, the reinforcing element can be a pledget. Pledgets are generally buttressing or cushioning pads through which a flexible connector (e.g., a flexible cord) can be threaded, in order to prevent the flexible connector from cutting into the tissue. The reinforcing element may include a top surface and a bottom surface, and can be configured in a variety of sizes and shapes, including rectangular, circular, elliptical, etc. For example, in certain embodiments the length of the reinforcing element ranges from 1 mm to 10 mm, such as from 1 mm to 8 mm, or 1 mm to 5 mm. The width of the reinforcing element in some cases ranges from 1 mm to 10 mm, such as from 1 mm to 8 mm, or 1 mm to 5 mm. In some embodiments, the thickness of the reinforcing element ranges from 0.1 mm to 2 mm, such as from 0.1 mm to 1.0 mm, or 0.1 mm to 0.5 mm.

A reinforcing element can be made of any suitable material (e.g., a biocompatible material). Such a material may be a flexible or rigid material. By "rigid", as used herein is meant non-pliable or not capable of being bent or flexed (e.g., bent or flexed with a force exerted by a human hand or other body part) without sustaining damage. A rigid material may be a material that remains able to perform its intended function (e.g., remaining in a substantially fixed position) by remaining stiff (e.g., resistant to force exerted on it by a human hand or other body part) for at least the expected lifetime or useful lifetime of the aspect in which the material is included. In some embodiments, reinforcing elements are composed of one or more materials that are rigid or otherwise strong enough to resist pull-through by the flexible connector to which they are mounted. In some embodiments, a reinforcing element is made of a sufficiently soft and flexible material to effectively prevent damage to the tissue, e.g., a papillary muscle. In some embodiments, reinforcing elements are composed of one or more materials that are pierce-able by a needle (e.g., a needle advanced through the material by a human hand and with the force normally exerted by a human hand in pushing a needle through a material).

Reinforcing elements may be composed of biocompatible polymers and/or metals. In various embodiments, reinforcing elements include fabrics such as felt (e.g., polyester felt) and/or polyester. In some embodiments, reinforcing elements include polytetrafluoroethylene, polytetrafluoroethylene(PTFE), expanded PTFE, or any of the other materials (e.g., biocompatible materials) listed herein, or any combinations thereof. In certain embodiments, an active agent is included in the composition of a biocompatible material of the reinforcing element. In some embodiments, the one or more active agents include an antithrombotic substance and/or an antibiotic substance and/or an anti-inflammatory (e.g., a substance that reduces or prevents inflammation). In various embodiments, a reinforcing element may be coated with a polymer, such as a polymer that releases one or more active agents (e.g., an anticoagulant that thereby reduces the risk of thrombus formation). In some embodiments, the reinforcing element does not include a tissue piercing member (e.g., a needle).

In addition, the reinforcing element can include one or more (e.g., one, two, three, four, etc.) openings through which the flexible connector element may pass. In other embodiments, the flexible connector is attached to the reinforcing element without passing through an opening, e.g., the flexible connector has been pulled through with a needle. In some embodiments, the reinforcing element is mounted such that it is substantially fixed (e.g., adhesively attached and/or tied) in a position on the flexible connector. For example, the reinforcing element can be sewn, or glued, or fused in any suitable manner so that it is fixed in position on the flexible connector, e.g., fixed in position at or substantially at the first or second ends of the flexible connector. In other embodiments, the reinforcing element is mounted such that it is slidably mounted on a flexible connector. By "slidably" is meant that the reinforcing element is attached to the flexible connector so that it is secure yet it is possible to move the reinforcing element along at least part of the length of the connector. For example, a flexible connector can have a reinforcing element (e.g., a pledget) initially positioned halfway between the first and second ends of the flexible connector. In using the synthetic chord device, it may be desirable to move the reinforcing element to a position closer to the first or second end before securing the reinforcing element to a tissue.

Specific Embodiments

Figure 1B:

FIGS. 1A to 1B provide side and top views of a synthetic chord device prior to deployment, according to an embodiment of the invention. As shown in FIG. 1A, synthetic chord device 100 includes a first flexible connector 102 having a pledget 104 at a second end. Device 100 further includes a curved needle 110 connected to an elongated shape memory coil 112 by a second flexible connector 114. Also shown is removable sheath 108 which is configured to maintain the elongated shape memory coil 112 in a linear configuration when present inside of the sheath. As shown, the proximal end 106 of elongated shape memory coil is outside of the proximal end of sheath 108 and has assumed a relaxed, loop configuration. It is noted that, upon use, when passed through the first tissue this proximal end 106 straightens out in response to resistance from the first tissue so as to readily pass through the first tissue with the rest of the sheathed portion of the device. Sheath 108 further includes two markings, i.e., a first proximal end band 116 of different color from the majority of the sheath, where the band has a width that approximates the width of the tissue through which the securing member is to pass and therefor provides an indication to a user of when to stop moving the sheath through the tissue, and a second distal end stripe 118 of different color from the majority of the sheath which indicates where a user should cut the sheath 108 to release the needle 110 following placement. As shown in FIG. 1A, the distal end of sheath 108 is stably associated with second flexible connector 114 at location 120. FIG. 1B provides a view of the device depicted in FIG. 1A as seen along line A-A as indicated in FIG. 1A. As can be seen in FIG. 1B, first flexible connector 102 is made up of two strands, which strands connect the reinforcing pledget 104 to the elongated shape memory coil 112 present in the sheath 108.

Figure 1C:
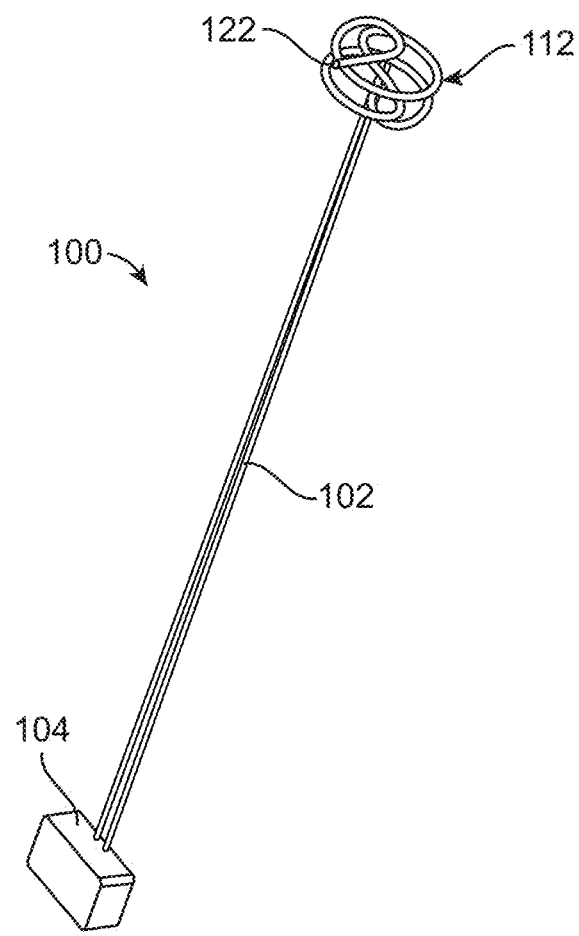
FIG. 1C provides a view of the device shown in FIGS. 1A and 1B when present in a deployed state.

FIG. 1C shows the device of FIGS. 1A and 1B in a deployed state, i.e., following removal of the curved needle and the removable sheath. As shown in FIG. 1C, device 100 includes dual strand flexible connector 102 having pledget 104 at its proximal end and stacked dual-loop attachment element 112 at its distal end. As can be seen in FIG. 1C, stacked dual-loop attachment element includes first and second loops which are in different orientations. As the first and second loops are in opposite orientations, beginning at distal end 122, the first loop of the coil spirals in a first orientation and then the coil spirals in a second orientation in the second loop.

In certain the embodiments described above, the devices include a first flexible connector and, optionally a second flexible connector. In some instances, the devices may include a third flexible connector. In these embodiments, the third flexible connector may be attached to the reinforcing element at a first end. A second attachment element may be present at the other end of the third flexible connector. As with the first attachment element, the second attachment element includes tissue piercing member and a securing member, optionally separated from each other by a fourth flexible connector. In these embodiments, the reinforcing element may be stably attached to the first ends of the first and third flexible members. Alternatively, the reinforcing element may be slidably attached to the first and third flexible members.

Where desired, the first and third flexible members form a continuous flexible structure or connector. In these embodiments where the device includes first and second attachment elements, the synthetic chord device may be described as one that includes a single flexible connector having an attachment element at both a first end and a second end of the flexible connector, wherein each attachment element includes a tissue piercing member coupled to a securing member and where each of the attachment elements is configured such that separation of the piercing member from the securing member results in a transition of the securing member from a linear to planar configuration, e.g., as described above. At least a portion of the flexible cord can be configured to be secured to a second tissue, e.g., may include a pledget, such as described above.

Methods

Synthetic chord devices, e.g., as described above, find use in methods for connecting a first tissue, such as a cardiac valve leaflet, to a second tissue, such as a papillary muscle. The subject devices therefore find use in methods in which a prolapsed cardiac valve leaflet, such as a mitral valve leaflet, is repaired. The subject devices can be used in an open surgical procedure, a minimally invasive surgical procedure, an endovascular procedure, or other interventional procedure.

Methods for repair of a cardiac valve, such as a mitral valve, are discussed below. When performing a conventional heart valve repair procedure, incisions may be made into the thoracic cavity and pericardium, and then into aorta or myocardium in order to have access to the damaged heart valve. The procedure may be an open procedure in which the sternum is opened and the ribs are spread with a conventional retractor, or a minimally invasive procedure, e.g., wherein the heart and heart valve are accessed through minimally invasive openings in the thoracic cavity, such as through trocar cannulas or small incisions in the intercostal spaces, via blood vessels, etc. The minimally invasive procedures can be viewed remotely using a camera and monitor, or in some cases directly, as desired.

Figure 2:
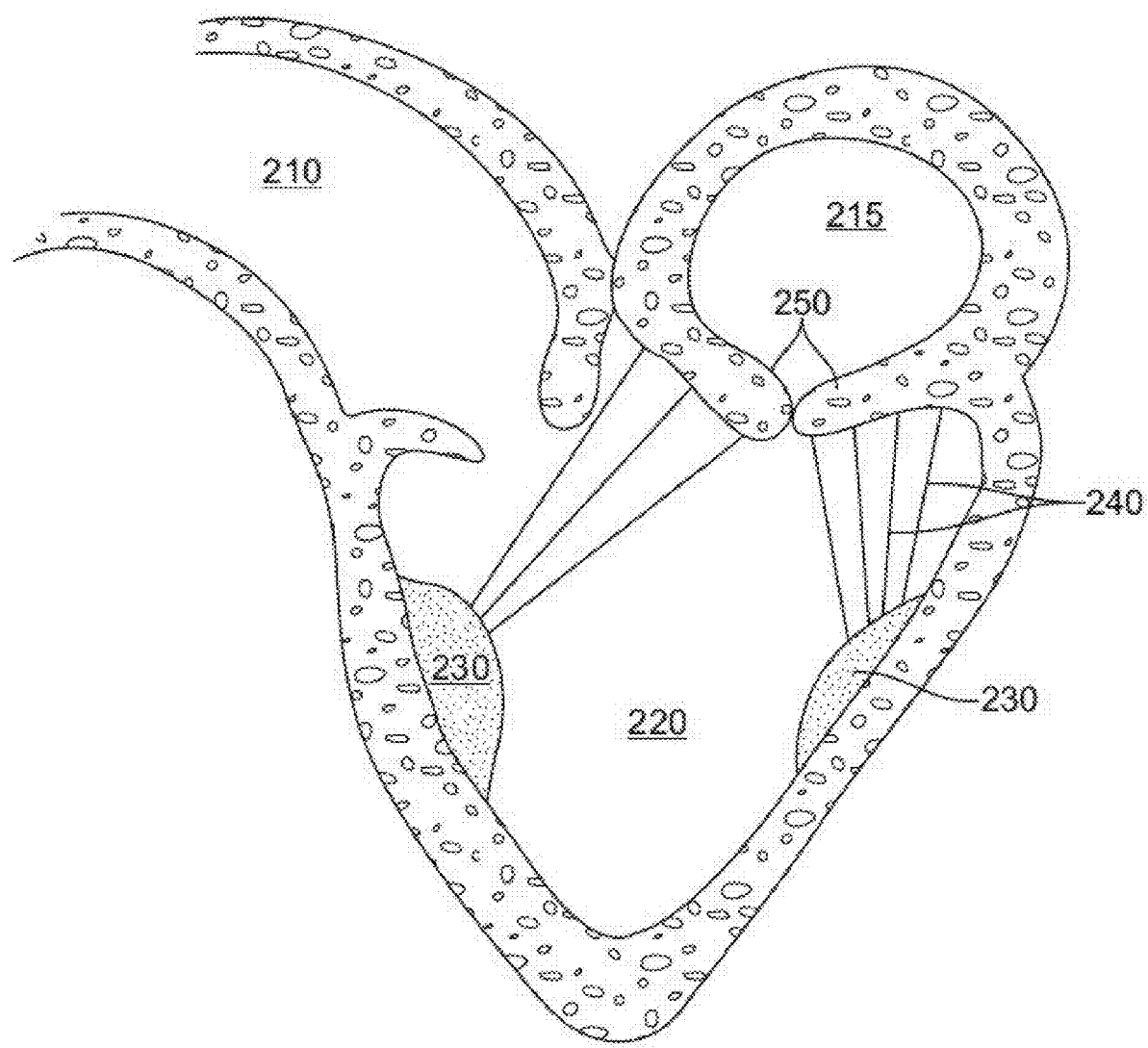
FIG. 2 provides a schematic view of the normal left side of the heart.

FIG. 2 depicts a schematic drawing of the left side of the heart. The aortic arch 210, left atrium 215, and left ventricle 220 are shown, with the mitral valve 250 located between the left ventricle and the left atrium. The chordae tendineae are shown as elements 240, attached to the leaflets of the mitral valve on one end, and the papillary muscle 230 in the left ventricle on the other end.

After exposure of the mitral valve and the subvalvular area, the desired length of the flexible connector (e.g., first flexible connector), is determined by measuring the distance between the second tissue (e.g., the prolapsed leaflet) and the first tissue (e.g., the cardiac tissue located below the prolapsed mitral valve leaflet, such as, for example, the papillary muscle) using methods that are well known in the art. The desired length for the flexible connector can be determined using any suitable measuring device, such as a caliper, or a Mohr Suture Ruler Device™ (Geister, Tuttlingen, Germany). For example, a caliper or sterile disposable flexible tape measure can be used to assess the correct length for the synthetic mitral valve chordae by measuring the distance between the tip of the papillary muscle and the edge of a non-prolapsing segment of the mitral valve leaflet. The measurement can also be confirmed by comparison with pre-operative transesophageal echocardiography (TEE).

Figure 3:
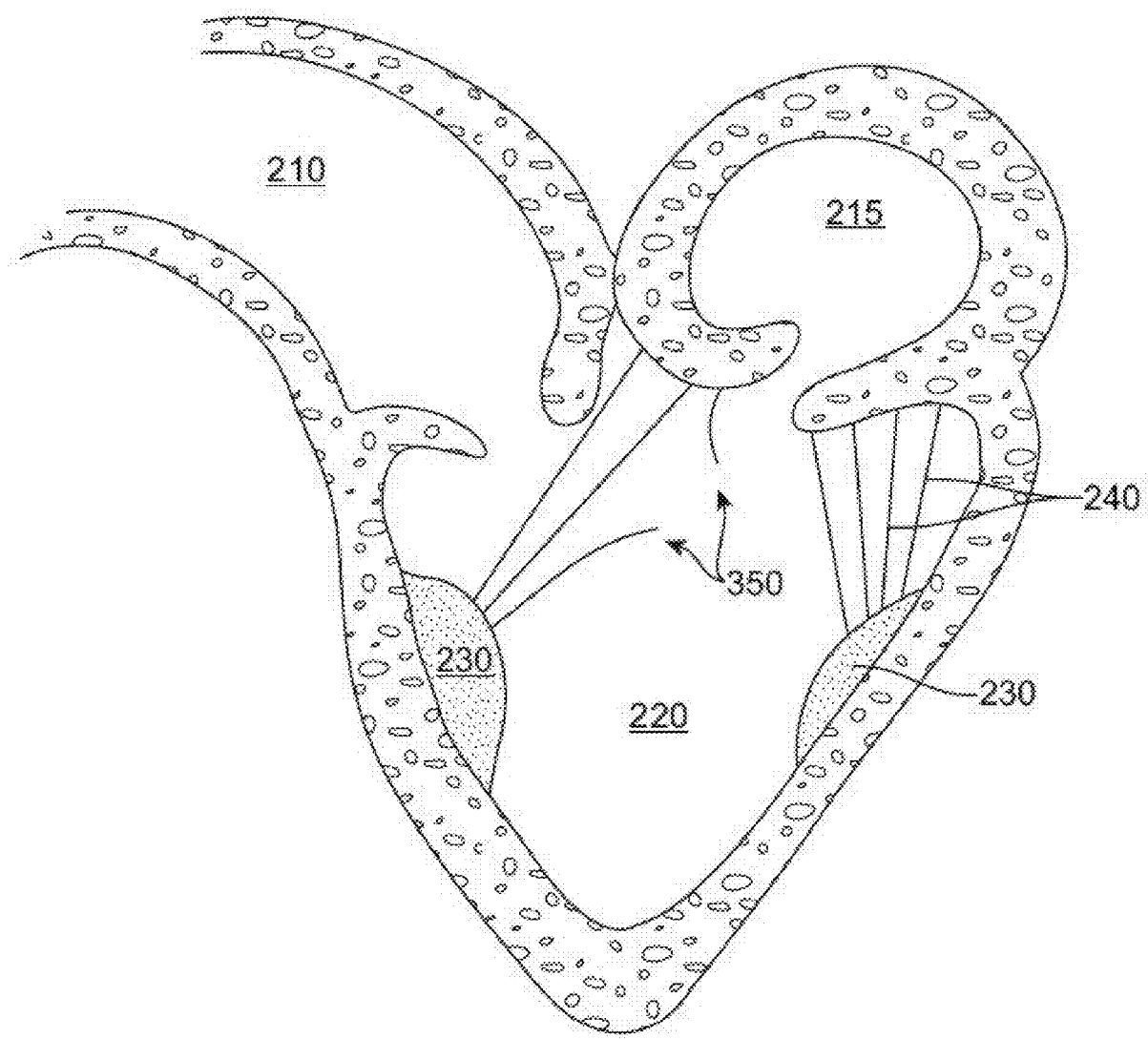
FIG. 3 provides a schematic view of the left side of the heart demonstrating a ruptured chorda tendineae of the mitral valve.

An illustration of a rupture, or breakage of one of the chorda tendineae that can be repaired using the methods and devices of the subject invention is shown in FIG. 3. FIG. 3 depicts a schematic drawing showing portions of the heart including the aortic arch 210, left atrium 215, and left ventricle 220, with the mitral valve 250 located between the left ventricle and the left atrium. The chordae tendineae are shown as elements 240, attached to the leaflets of the mitral valve on one end, and the papillary muscle 230 in the left ventricle on the other end. The ruptured, or broken chorda tendineae is shown as element 350. The leaflets of the mitral valve now no longer coapt, or close, and during systole, blood can flow from the left ventricle back into the left atrium, i.e., mitral regurgitation.

If a set of synthetic chord devices is provided, the synthetic chord device having a first flexible connector with the desired length, or the closest to the desired length, is then selected from among the set of synthetic chord devices. The set of synthetic chord devices can include two or more first flexible connectors of the same or of different lengths, such as three connectors, or four connectors, etc. If a set of synthetic chord devices is not provided, but instead, an appropriate single synthetic chord device is available, that synthetic chord device is selected for use.

The tissue piercing member on the first end, e.g., a needle, is first passed (e.g., advanced) through a first tissue, such as the cardiac tissue below the prolapsed mitral valve leaflet, e.g., a papillary muscle, and pulled through until the reinforcing element, e.g., a pledget, is in substantial contact with a surface of the first tissue, e.g., papillary muscle. The tissue piercing member, e.g., the needle, is then passed through a second tissue, such as the leaflet of the prolapsed mitral valve, until the securing member has passed at least partially into or through the second tissue, such as the leaflet.

The position of the prolapsed valve leaflet may be adjusted by coordinating the tension of the first flexible connector and the location of the leaflet. For example, a practitioner (e.g., a doctor, surgeon, technician, etc.) may move the prolapsed valve into a correct (e.g., non-prolapsed) position by adjusting the position of the valve leaflet directly by pushing against the anchor attached to the valve leaflet (e.g., using the securing member to push against the anchor and applying tension to the connector). The valve leaflet position may be adjusted in real-time in a beating heart (e.g., using echocardiography). For example, the valve leaflet may be repositioned while monitoring mitral regurgitation (MR). Once any MR is reduced or eliminated, the valve leaflet is in the correct position.

Once the valve leaflet is positioned correctly, the securing member can then be deployed (e.g., by separating the needle and removing the sheath) to transition the securing member to the stacked, dual loop configuration and thereby connect a second tissue (e.g., a cardiac valve leaflet) to a first tissue (e.g., a papillary muscle) by the flexible connector. It should be noted that the number of synthetic chord devices required to secure the connecting tissues together may vary depending on the procedure and the anatomy.

Figure 4:
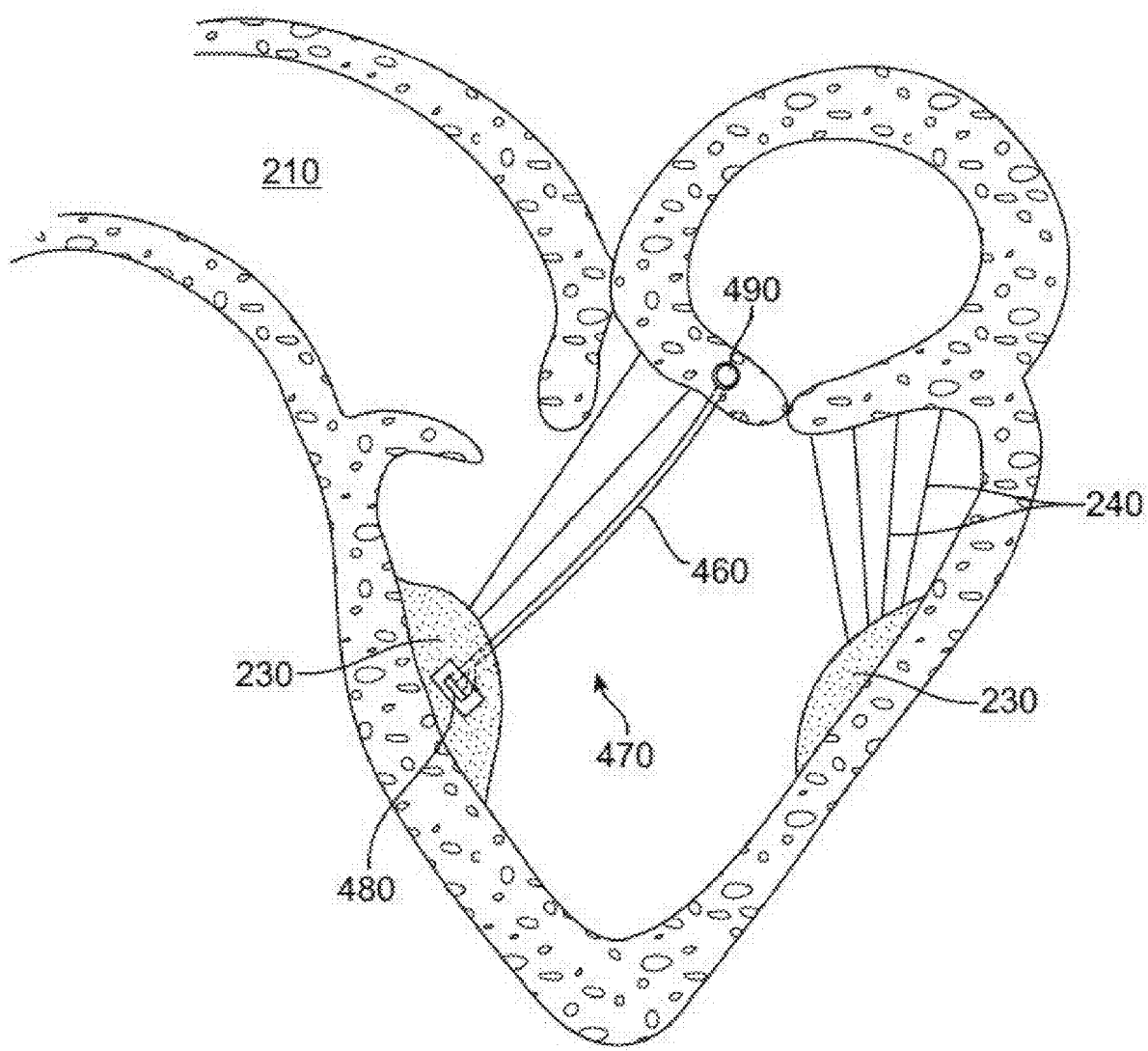
FIG. 4 provides a schematic view of the left side of the heart after repair of the ruptured chorda tendineae of the mitral valve with embodiments of the synthetic chord device of the subject invention.

FIG. 4 shows an embodiment of a repair of the ruptured chorda tendineae with a synthetic chord device 470 of the subject invention. FIG. 4 illustrates the first flexible connector 460 attached to the mitral valve leaflet at one end with securing member 490, which in this embodiment has spiral planar configuration. Securing member 490 is shown in a deployed planar configuration. First flexible connector 460 is also shown secured to the tissue below the mitral valve leaflet (e.g., the papillary muscle) with reinforcing element 480. After repair, the leaflets of the mitral valve 250 now coapt, or close, and blood can no longer flow from the left ventricle back into the left atrium during systole.

By this method, a prolapsed mitral valve leaflet can be repaired by securing the leaflet to the papillary muscle below. Using the methods and devices of the subject invention, a mitral valve repair procedure can be successfully completed without the need for the time-consuming step of cutting the desired length of synthetic cord while the patient is on the operating table, thereby decreasing the amount of time needed to place a patient on cardio-pulmonary bypass. In addition, the subject methods and devices obviate the need for tying sutures and ensuring that the suture material does not become tangled, difficulties which are exacerbated by the small size of the tissues involved and the often limited field of the operation.

Any appropriate prolapsed valve leaflet may be treated as described herein, including mitral valve leaflets and tricuspid valve leaflets. Further, these methods may be performed using one or more catheters or using non-catheter surgical methods, or using a combination of catheter-type surgical methods and non-catheter type surgical methods. The methods of the subject invention may also be used in combination with other surgical procedures, e.g. replacement of a mitral valve annulus, etc.

In some variations, the first flexible connector may be advanced via one or more catheters to the proximity of the prolapsed valve leaflet in an anterograde approach (e.g., from above the mitral valve). Alternatively, the first flexible connector may be advanced via a retrograde approach (e.g., from below the mitral valve). In all of the methods described herein, the cardiac tissue located below the prolapsed valve (to which a reinforcing element is attached) may be selected from the group consisting of a papillary muscle and a ventricular wall.

The subject methods also include the step of diagnosing a patient in need of cardiac valve repair, e.g., mitral valve repair. Primary mitral regurgitation is due to any disease process that affects the mitral valve device itself. The causes of primary mitral regurgitation include myxomatous degeneration of the mitral valve, infective endocarditis, collagen vascular diseases (e.g., SLE, Marfan's syndrome), rheumatic heart disease, ischemic heart disease/coronary artery disease, trauma balloon valvulotomy of the mitral valve, certain drugs (e.g. fenfluramine). If valve leaflets are prevented from fully coapting (i.e., closing) when the valve is closed, the valve leaflets will prolapse into the left atrium, which allows blood to flow from the left ventricle back into the left atrium, thereby causing mitral regurgitation.

The signs and symptoms associated with mitral regurgitation can include symptoms of decompensated congestive heart failure (e.g., shortness of breath, pulmonary edema, orthopnea, paroxysmal nocturnal dyspnea), as well as symptoms of low cardiac output (e.g., decreased exercise tolerance). Cardiovascular collapse with shock (cardiogenic shock) may be seen in individuals with acute mitral regurgitation due to papillary muscle rupture or rupture of a chorda tendinea. Individuals with chronic compensated mitral regurgitation may be asymptomatic, with a normal exercise tolerance and no evidence of heart failure. These individuals however may be sensitive to small shifts in their intravascular volume status, and are prone to develop volume overload (congestive heart failure).

Findings on clinical examination depend of the severity and duration of mitral regurgitation. The mitral component of the first heart sound is usually soft and is followed by a pansystolic murmur which is high pitched and may radiate to the axilla. Patients may also have a third heart sound.

Patients with mitral valve prolapse often have a mid-to-late systolic click and a late systolic murmur.

Diagnostic tests include an electrocardiogram (EKG), which may show evidence of left atrial enlargement and left ventricular hypertrophy. Atrial fibrillation may also be noted on the EKG in individuals with chronic mitral regurgitation. The quantification of mitral regurgitation usually employs imaging studies such as echocardiography or magnetic resonance angiography of the heart. The chest x-ray in patients with chronic mitral regurgitation is characterized by enlargement of the left atrium and the left ventricle. The pulmonary vascular markings are typically normal, since pulmonary venous pressures are usually not significantly elevated. An echocardiogram, or ultrasound, is commonly used to confirm the diagnosis of mitral regurgitation. Color doppler flow on the transthoracic echocardiogram (TTE) will reveal a jet of blood flowing from the left ventricle into the left atrium during ventricular systole. Because of the difficulty in getting accurate images of the left atrium and the pulmonary veins on the transthoracic echocardiogram, a transesophageal echocardiogram (TEE) may be necessary to determine the severity of the mitral regurgitation in some cases. The severity of mitral regurgitation can be quantified by the percentage of the left ventricular stroke volume that regurgitates into the left atrium (the regurgitant fraction). Other methods that can be used to assess the regurgitant fraction in mitral regurgitation include cardiac catheterization, fast CT scan, and cardiac MRI.

Indications for surgery for chronic mitral regurgitation include signs of left ventricular dysfunction. These include an ejection fraction of less than 60 percent and a left ventricular end systolic dimension (LVESD) of greater than 45 mm.

Kits

Also provided are kits that at least include the subject devices. The subject kits at least include a synthetic chord device of the subject invention and instructions for how to use the synthetic chord device in a procedure. In some embodiments, the kits can include a set of two or more synthetic chord devices. In other embodiments, a set of synthetic chord devices can include at least three synthetic chord devices, e.g., four or more, five or more, six or more, etc.

In some embodiments, a set of synthetic chord devices includes two or more synthetic chord devices in which at least two of the synthetic chord devices have flexible connectors (e.g., first flexible connectors and/or one or more first flexible connectors and/or one or more second flexible connectors) of different lengths. In other embodiments, the flexible connector (e.g., first flexible connector) portions of the synthetic chord devices are all of differing lengths. In some embodiments, a set of synthetic chord devices can have two or more synthetic chord devices in which the flexible connectors (e.g., first flexible connectors) are of the same length. A set of synthetic chord devices can therefore have two or more some synthetic chord devices in which some are of the same length, and some are of a different length. For example, in one embodiment a set of six synthetic chord devices can have two synthetic chord devices in which the flexible connector (e.g., first flexible connector) portion is 8 mm in length; two synthetic chord devices in which the flexible connector portion is 10 mm in length; and two synthetic chord devices in which the flexible connector portion is 12 mm in length. In another embodiment, a set of synthetic chord devices can have four synthetic chord devices in which the flexible connector (e.g., first flexible connector) in all of them is 10 mm in length.

In addition, in some embodiments, the synthetic chord devices can be color-coded, such that a desired length of the synthetic mitral valve chord, or flexible connector (e.g., first flexible connector) element, can be easily determined. For example, a package with multiple synthetic chord devices can have flexible connectors (e.g., first flexible connectors) of two different colors arranged in an alternating pattern to allow a medical practitioner (e.g., scrub nurse) to readily distinguish one synthetic chord device from another. For example, a set of ten synthetic chord devices in a kit can be arranged in two horizontal rows of five in each row. An exemplary arrangement of associated flexible connector colors would be, in the top row: white, green, white, green, white, and in the bottom row: green, white, green, white, green. Further details of packaging that can be adapted for use with the synthetic chord devices of the subject invention are disclosed in U.S. Pat. No. 6,029,806, incorporated herein by reference. In this manner, a scrub nurse can readily associate each tissue piercing member (e.g., needle) with the synthetic chord device containing the correct length of synthetic mitral valve chord, or flexible connector. By color coding the synthetic chord devices with alternating, contrasting flexible connector colors, more synthetic chord devices can be stored in a package of a given size without causing confusion. The needle associated with each synthetic chord device can be sufficiently separated from other such needles to allow grasping of each needle with a needle holder, while maintaining identification of the needle as belonging to the same synthetic chord device.

The kit can also include a measuring tool, which can be disposable, for determining a desired length of a synthetic chord by measuring a desired distance, such as the distance between a prolapsed cardiac valve leaflet and cardiac tissue located below the prolapsed cardiac valve leaflet. Such a measuring tool may include, but is not limited to any suitable measuring device, such as a caliper, a Mohr Suture Ruler Device™ (Geister, Tuttlingen, Germany), or sterile disposable flexible tape measure.

The instructions for using the devices as discussed above are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g., portable flash drive, DVD- or CD-ROM, etc. The instructions may take any form, including complete instructions for how to use the device or as a website address with which instructions posted on the world wide web may be accessed.

The following example is offered by way of illustration and not by way of limitation.

EXPERIMENTAL

A patient is prepared for a mitral valve prolapse repair procedure in a conventional manner. The patient is anesthetized using conventional anesthesia and anesthesiology procedures.

The patient undergoes an intraoperative transesophageal echocardiography to determine the mechanism of the mitral regurgitation (MR), and to estimate the required length for the synthetic mitral valve neochordae. The intraoperative transesophageal echocardiography also serves as a baseline evaluation for assessing the quality of the repair, and for follow-up evaluation.

The patient's skin overlying the sternum and surrounding areas is swabbed with a conventional disinfecting solution. Next, the surgeon accesses the patient's thoracic cavity via a right anterolateral mini-thoracotomy, through a 3 cm incision. Three additional small 10 mm ports are made for video camera, a left atrial retractor, and a transthoracic aortic clamp.

The heart is then accessed by opening the pericardium. Next, the patient is placed on cardiopulmonary bypass in a conventional manner and the patient's heart is stopped from beating in a conventional manner. The surgeon then performs the mitral valve repair in the following manner: The valve is accessed through an incision in the left atrium or across the atrial septum if bi-caval cannulation is utilized for cardiopulmonary bypass. After exposure of the mitral valve and the subvalvular area, the desired length of the flexible connector (e.g., first flexible connector), is determined by measuring the distance between the tip of the papillary muscle and the edge of a non-prolapsing segment of the mitral valve leaflet.

A synthetic chord device as depicted in FIGS. 1A-1B is selected from a set of synthetic chord devices of the present invention based on the measurement. The needle is advanced through the papillary muscle located below the mitral valve leaflet, and pulled through until the reinforcing element (e.g., pledget) is in substantial contact with a surface of the papillary muscle. The needle is then advanced through the leaflet of the prolapsed mitral valve until the proximal end band of the sheath appears visible at the top of the leaflet surface. The sheath is then clipped at the distal end strip, thereby releasing the needle. Finally, the sheath is manually separated from the remainder of the device so that the securing member deploys such that a first loop is above the leaflet and a second loop is below the leaflet.

Post-repair valve competency can be assessed by filling and pressurizing the left ventricle with saline and observing the valve. The incisions are then closed and the patient weaned, or removed, from cardiopulmonary bypass. After weaning the patient from cardiopulmonary bypass, valve function is examined with transesophageal echocardiography or like means. The chest and skin incisions are then closed to complete the procedure.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A synthetic chord comprising:
    (a) a flexible connector comprising a first end and a second end and an axis along a length between the first end and the second end;
    (b) an attachment element comprising a tissue piercing member and a securing member stably associated with the first end of the flexible connector, wherein the securing member comprises an elongated shape memory coil that is present in a removable sheath having a proximal and distal end and configured to maintain elongation of the shape memory coil, and wherein a portion of the elongated shape memory coil is configured to assume a stacked multi-loop configuration with at least two stacked loops looped around the axis when said portion of the elongated shape memory coil is present in a relaxed state outside of the removable sheath;
    (c) wherein said at least two stacked loops have a spiraling form, spiraling in opposite directions;
    (d) wherein said stacked multi-loop configuration includes a free end opposite an attached end, said attached end attached to said first end of said flexible connector;
    (e) wherein said free end of said stacked multi-loop configuration extends radially before extending circumferentially toward said attached end; and
    (f) a reinforcing element located at the second end of the flexible connector.

2. The synthetic chord according to claim 1, wherein the stacked multi-loop configuration comprises two stacked loops.

3. The synthetic chord according to claim 1, wherein the elongated shape memory coil comprises a shape memory material.

4. The synthetic chord according to claim 3, wherein the shape memory material is a metal alloy.

5. The synthetic chord according to claim 1, wherein the elongated shape memory coil comprises a central shape memory wire present in a casing.

6. The synthetic chord according to claim 5, wherein the casing is fabricated from a material that promotes tissue ingrowth.

7. The synthetic chord according to claim 1, wherein the tissue piercing member comprises a needle.

8. The synthetic chord according to claim 1, wherein the securing member and tissue piercing member of the attachment element are separated from each other by a second flexible connector.

9. The synthetic chord according to claim 8, wherein the distal end of the removable sheath is stably associated with the second flexible connector.

10. The synthetic chord according to claim 1, wherein prior to deployment in a patient, the securing member has a proximal elongated end present in the removable sheath and a coiled proximal end outside of the proximal end of the removable sheath.

11. The synthetic chord according to claim 1, wherein the securing member further comprises a stabilizer for maintaining the elongated shape memory coil about tissue upon deployment.

12. The synthetic chord according to claim 11, wherein the stabilizer comprises a barb.

13. The synthetic chord according to claim 1, wherein the reinforcing element is a pledget.

14. The synthetic chord of claim 1, wherein said opposite directions of said at least two stacked loops include a clockwise orientation and a counterclockwise orientation.

15. The synthetic chord of claim 1, wherein said at least two stacked loops each include a majority of at least one full turn.

16. The synthetic chord of claim 15, wherein at least one of said at least two stacked loops includes a full turn.

17. The synthetic chord of claim 1, wherein said at least two stacked loops include an S-curve segment therebetween.

18. A method for connecting a first tissue to a second tissue in a patient, the method comprising:
(a) passing the tissue piercing member of the synthetic chord according to claim 1 through the first tissue so that the reinforcing element contacts the first tissue;
(b) passing the tissue piercing member through the second tissue so that the securing member spans the second tissue;
(c) removing the removable sheath so that the portion of the elongated shape memory coil assumes the stacked multi-loop configuration with at least two stacked loops looped around the axis of the flexible connector with the at least two stacked loops having the spiraling form, spiraling in opposite directions to deploy about the second tissue in a manner sufficient for the synthetic chord to connect the first tissue to the second tissue;
(d) wherein said removing step includes the stacked multi-loop configuration having the free end opposite the attached end, the attached end attached to the first end of the flexible connector, and
(e) wherein said removing step includes the free end of the stacked multi-loop configuration extending radially before extending circumferentially toward the attached end.

19. The method of claim 18, wherein the opposite directions of the at least two stacked loops include a clockwise orientation and a counterclockwise orientation.

20. A kit comprising: a set of two or more synthetic chords according to claim 1.

* * * * *